United States Patent
Bardoni

(10) Patent No.: US 10,041,917 B2
(45) Date of Patent: Aug. 7, 2018

(54) GAS DETECTION SYSTEM FOR TOXIC AND/OR FLAMMABLE GAS

(71) Applicant: IMX S.R.L., Cinisello Balsamo (IT)

(72) Inventor: Giovanni Mario Bardoni, Bresso (IT)

(73) Assignee: IMX S.R.L., Balsamo (IT)

( * ) Notice: Subject to any disclaimer, the term of this patent is extended or adjusted under 35 U.S.C. 154(b) by 0 days.

(21) Appl. No.: 15/117,604

(22) PCT Filed: Aug. 3, 2015

(86) PCT No.: PCT/IB2015/001329
§ 371 (c)(1),
(2) Date: Aug. 9, 2016

(87) PCT Pub. No.: WO2016/030735
PCT Pub. Date: Mar. 3, 2016

(65) Prior Publication Data
US 2017/0138918 A1 May 18, 2017

(30) Foreign Application Priority Data
Aug. 8, 2014 (IT) .............................. MI2014A1484

(51) Int. Cl.
*G01N 33/00* (2006.01)

(52) U.S. Cl.
CPC ..... *G01N 33/0031* (2013.01); *H04Q 2209/40* (2013.01); *H04Q 2209/60* (2013.01)

(58) Field of Classification Search
CPC ........... G01N 33/0031; G01N 33/0036; G01N 33/0057; G01N 33/005; G01N 33/0052; G01N 33/0054; G01N 33/0055
See application file for complete search history.

(56) References Cited

U.S. PATENT DOCUMENTS

| | | | | | |
|---|---|---|---|---|---|
| 4,464,653 A | * | 8/1984 | Winner | ................ | G01D 18/008 324/464 |
| 4,555,930 A | * | 12/1985 | Leach | .................. | G01N 27/122 73/1.07 |

(Continued)

FOREIGN PATENT DOCUMENTS

| | | |
|---|---|---|
| EP | 1197753 A2 | 4/2002 |
| EP | 1544614 A1 | 6/2005 |
| WO | 2011053721 A1 | 5/2011 |

OTHER PUBLICATIONS

"Overview of 1-Wire Technology and Its Use." Dallas Semiconductor, Application Note 1796, Dec. 2002. <http://hivetool.org/w/images/e/e5/1-wire.pdf> Accessed Jan. 9, 2018.*

*Primary Examiner* — Harshad R Patel
*Assistant Examiner* — Punam Roy
(74) *Attorney, Agent, or Firm* — Hoffmann and Baron, LLP

(57) ABSTRACT

The present invention relates to the field of detection of combustible, flammable and toxic gases present in the air, particularly any way generated by pipe leaks, such as leaks of gaseous hydrocarbons or evaporation or similar potentially toxic and/or explosive gases. For example a sector object of the present invention is the gas environmental detection, more particularly for safety and protection of operators in gas drilling, extraction, transport and stocking. The present invention described a system of detection of flammable and/or toxic gases, comprising detection elements able to increase the reliability of detection of said elements dangerous for both human beings and the environment.

11 Claims, 10 Drawing Sheets

(56) References Cited

U.S. PATENT DOCUMENTS

| | | | | |
|---|---|---|---|---|
| 4,608,552 | A * | 8/1986 | Boutonnat | G01N 33/0062 340/12.37 |
| 4,896,526 | A * | 1/1990 | Ratfisch | G01N 27/626 340/632 |
| 5,025,653 | A * | 6/1991 | Schuldt | G01N 33/0032 73/23.2 |
| 5,200,743 | A * | 4/1993 | St. Martin | H04Q 9/14 340/12.37 |
| 5,305,231 | A * | 4/1994 | Coppler | G01N 33/0008 702/24 |
| 5,439,414 | A * | 8/1995 | Jacob | B08B 15/023 454/61 |
| 5,786,768 | A * | 7/1998 | Chan | G08B 7/06 340/540 |
| 6,357,034 | B1 * | 3/2002 | Muller | G08C 15/00 714/746 |
| 6,611,208 | B1 * | 8/2003 | Ketler | G08B 17/10 340/534 |
| 7,132,659 | B2 * | 11/2006 | Starta | G01N 21/3504 250/341.5 |
| 9,851,772 | B2 * | 12/2017 | Dwelley | G06F 1/3206 |
| 2005/0280408 | A1 * | 12/2005 | Wobschall | G01D 3/022 324/115 |
| 2006/0012491 | A1 * | 1/2006 | Mahowald | H04Q 9/00 340/870.02 |
| 2007/0206521 | A1 * | 9/2007 | Osaje | G01D 4/004 370/315 |
| 2012/0192623 | A1 | 8/2012 | Adami et al. | |
| 2015/0068287 | A1 * | 3/2015 | Wilcox | G01M 3/22 73/40.5 R |

* cited by examiner

| SENSORS | POSSIBLE COMBINATIONS OF GASES | | SENSITIVE ELEMENTS |
|---|---|---|---|
| REDUNDANT | FLAMMABLE | CAT+CAT | DOUBLE CATALYTIC |
| REDUNDANT | TOXIC | nMos+nMos | DOUBLE NANOMOS |
| REDUNDANT | TOXIC | E.C.+E.C. | DOUBLE ELECTROCHEMICAL |
| REDUNDANT | HYDROCARBONS | I.R.+I.R. | DOUBLE INFRERED |
| DOUBLE TECHNOLOGY | FLAMMABLE+TOXIC | CAT+nMos | CATALYTIC +NANOMOS |
| DOUBLE TECHNOLOGY | FLAMMABLE+TOXIC | CAT+E.C. | CATALYTIC+ELECTROCHEMICAL |
| DOUBLE TECHNOLOGY | FLAMMABLE+HYDROCARBONS | CAT+I.R. | CATALYTIC+INFRARED |
| DOUBLE TECHNOLOGY | TOXIC | nMos+E.C. | NANOMOS+ELECTROCHEMICAL |
| DOUBLE TECHNOLOGY | TOXIC+HYDROCARBONS | nMos+I.R | NANOMOS+INFRARED |
| DOUBLE TECHNOLOGY | TOXIC+HYDROCARBONS | E.C.+I.R. | ELECTROCHEMICAL+INFRARED |
| TRIPLE | TOXIC | nMos+nMos+nMos | TRIPLE NANOMOS |
| TRIPLE TECHNOLOGY | FLAMMABLE+TOXIC+HYDROCARBONS | CAT+Nmos+I.R. | CATALYTIC+NANOMOS+INFRARED |
| TRIPLE TECHNOLOGY | FLAMMABLE+TOXIC+HYDROCARBONS | CAT+E.C.+I.R. | CATALYTIC+ELECTROCHEMICAL+INFRARED |

Fig. 9

GAS DETECTION SYSTEM FOR TOXIC AND/OR FLAMMABLE GAS

This application is the U.S. National Phase of, and Applicants claim priority from, International Patent Application Number PCT/IB2015/001329 filed Aug. 3, 2015, which claims priority from MI2014A001484 filed Aug. 8, 2014, each of which is incorporated herein by reference.

BACKGROUND OF THE INVENTION

The present invention relates to the sector of combustible, inflammable and toxic gases present in the air, more particularly generated by leaks of pipes, for instance leaks of gaseous hydrocarbons or evaporation of potentially toxic and/or explosive gases. For instance a sector of interest for the present invention is the environmental detection of gases, more particularly for protection and safety of the operators of drilling, extraction, transport and stocking plants. Particular examples of hazardous environments certainly are oil processing places, such as rigs and/or gas extraction places or with high risk of presence of toxic or flammable gases, also produced by many industrial processes. Places of interest for the present invention are first of all drilling and lifting sea plants such as offshore rigs, and land plants like oil wells, where a possible gas escape contains a mixture consisting of flammable and toxic gases, more particularly H2S (hydrogen sulphide) which is extremely toxic even at very low concentration. This may happen also in chemical and petrochemical plants, in industries for transforming and stocking liquid and gaseous hydrocarbons or industries for conversion in other fuels such as hydrogen, ammonia and others.

Still of interest for the detection devices which will be hereinafter illustrated according to the present invention, is the detection of products converted as fuels containing toxic gases also in the liquid phase, which may release combustible and/or toxic gases, even at room temperature. Gases to be detected according to the present invention, for instance released in the atmosphere, may endanger in a particularly dangerous way the life of operators, and cause explosions as well, notwithstanding the existence of steady checks and safety measures, such as alarms and compulsory protective means, which unfortunately often result to be insufficient.

The present invention relates to innovative systems for detecting toxic or explosive gases, also comprising possible detecting and measuring devices for said systems. More particularly, the detection devices and systems proposed by the present invention are designed to solve the most serious and unfortunately well known problems of the prior art detection devices. More particularly, generally the detection systems available on the market for combustible and toxic gases for fixed installations, comprise only one kind of gas sensor for one detection technology only. Each sensor of this kind is generally connected to a single electronic transmitter. More particularly, this single channel detection aspect may possibly require presence of more detectors and in the best case this would anyway involve an increase of costs. In the worst case of one detector for a single gas, either because only one gas is indeed present in the environment or the possible arrangement of two detectors in the same room was not correctly done, the problems that may occur could be much more serious. Indeed, in case two or more gases are present in an area and the detectors are not correctly positioned (or two different kinds of detectors are not present), so that the presence of said two gases contemporaneously in the same area is not detected, in case of escape of one or more toxic and flammable gases, which individually would have only limited dangerous consequences, but when being together in the same environment, could produce toxic and even explosive mixtures, if said gases are not detected, the effects could be not only dangerous, but even devastating for persons and places, as known from news of explosions in factories and/or poisoning of individuals and the frequent fires and explosions of offshore rigs and land wells.

Moreover, a definitely considerable proportion of gas detectors available on the market have big problems due to the so-called fouling and clogging of the gas inlet filter of the sensor. This fouling problem involves false or even absent detections. This effect cannot be detected in sensors of the state of the art technology, because the filter is a component integral with the sensor body and this clogging status may be detected only with physical calibration text with sample gas. The experts in this field are aware that the possible use of compressed air to clear the filter, would only damage the sensitive element disposed after the filter. The sensor clogging drastically reduces the sensor response time, usually occurring by diffusion exploiting the gas partial pressures inside and outside the sensor. The sensor response time is certainly a factor of greater relevance for the timely recognition of possible dangers; clogging of filter is progressive as a function of the environment and it is definitely very onerous for applications on or near the sea, where salt deposit is a true hazard, because the sensor is prevented to alert the existence of danger, that as a rule requires an immediate and timely communication.

On the other hand clogging of filters often occurs in a very short time, and therefore this is still more dangerous for the correct operation of the detectors, more particularly but not exclusively on offshore rigs and in desert areas, where it frequently occurs that a sintered filter gets clogged by salt, fine powder or polluting agents also generating particulates in industrial areas.

In addition, the widespread sensors presently available on the market, like those well known and used by the oil companies and others operative in the oil and gas sector, have a sensor body and a sintered filter integral with said body, to be used in areas classified and subject to possible generation of explosive mixtures. When said filter becomes clogged, and people becomes aware that the filter is clogged, which is not easy in view of the place where the filter is installed, for safety reasons the filter must be changed even when it is only 50% clogged. The replacement operation involves high operative costs because one must replace the entire sensor, with which the filter is integral. Once the response time of the sensor has been found to be outside the standard parameters, said sensor must be replaced with high costs and times.

An illustrative example of the hereinbefore mentioned prior art problems can be found in document US 2012/0192623 A1 disclosing a classic system of gas detection comprising use of several kinds of sensors, carrying out individual measurements for a single type of gas and showing on a display said single measurement. In any case the display can show only one measure data. Moreover the type of sensor disclosed is a fixed sensor with sintered filter, which as above discussed cannot be cleaned and replaced individually, but the detection sensor must be replaced entirely, which is a very expensive operation, as already pointed out. Still more seriously, this type of sensors is a great danger for safety in the places that the sensor should theoretically keep safe; indeed said filters may be fully clogged, without showing any malfunctioning evidence even in the calibration stage, and this does not allow to obtain reliable reading and monitoring operations concerning the presence and concentration of those gases that said sensors should be able to detect, with possible tragic consequences like those above cited as prior art problems.

Some examples of detection or sensitive elements used in this sector are disclosed in document EP 1544614 illustrating an element sensitive to two gases, comprising two electrodes separated by a gasproof portion, detecting in this device for example carbon monoxide and hydrogen sulphide. This disclosure is moot about the complete sensor or the detection methods, the filter cleaning and so on. These sensitive elements are adapted to use with a broad range of assembled sensors, but the final reliability of the sensor is not depending from these elements, although they are efficient detectors to be used as a part of a larger device.

In a similar point of view of sensitive elements used or usable in this sector, document WO 2011/053721 discloses an electrochemical sensitive element comprising at least a first and a second gas detection electrode which are kept totally separate from each other as to the detection and the subsequent diffusion of gases detected inside the system, as well as for the subsequent transmission and recognition of the substance. The essential factor of this disclosure is an anti-diffusion barrier, that seems to be an important factor in the indicated sector. However in the sector of detecting gas for explosion danger, this factor is not very important because the gases to be detected are unfortunately already present mutually mixed in the surrounding air. In any case these sensitive elements cannot be compared with the gas detection devices, namely autonomous apparatus processing and generating the situation of danger that may occur.

Document EP 1197753 discloses a portable device for gas detection that may be attached to the human body, comprising a standard gas detection sensor, nothing is being stated for the safety problem in connection with fouling of sensors and the other problems hereinbefore discussed.

An object of the present invention is to provide for a detection system solving the above cited problems.

More particularly, an object of the present invention is to provide for a detection system with at least a double channel, allowing the contemporaneous detection of two or more gases.

Another object of the present invention is to provide for a system where the filter cleaning operation results to be simple and quick, and said cleaning substantially does not interrupt the sensor function of detecting continuously the possible presence of the gas at the installation place.

Connected thereto, it is also an object of the present invention to provide for a detection system with replaceable filters, without requiring replacement of the entire sensor body.

It is a further object of the present invention to optimize the production costs and the related costs for the users.

An essential object of the present invention is to increase safety and reliability of detection of toxic or flammable gases, in all the above cited sectors as well as other sectors where said system may be needed for safety purposes.

It is also an object of the present invention to provide for a detection system which should be performing, reliable, simple to be used as well as economically advantageous.

SUMMARY OF THE INVENTION

These and other objects will be achieved by the detection system according to the present invention, which is advantageously provided with two or more channels, as it will be described hereinafter, wherein the gas detection is carried out by a detection system comprising redundant or triple sensor and also contemporaneous measurements of flammable and/or toxic gases, with single or redundant detection of gases in the air, due to an escape of flammable and/or toxic gas or of both gases that when present at the same time may produce explosive and/or toxic mixtures.

In addition, in a further advantageous way, said detection system is provided with replaceable filters, thus allowing to optimize costs and limit waste, as well as to improve reliability of the detection instruments.

In particular this aspect, together with the other advantages hereinbefore described, and others that will be described hereinafter, increases considerably safety in said working places, which is the fundamental and definitely important object of the present invention, for safety of the operators.

Therefore object of the present invention is an innovative detection system for said toxic and/or combustible gases and more particularly their dangerous combinations, said system comprising at least a sensor body, a transducer and one or more gas detection sensitive elements.

The system described in the present invention, comprising two kinds of sensitive elements with two individual transducers in the same sensor, has the unique characteristic of detecting at the same time the two types of gas and signalling immediately their dangerousness. In addition to drilling plants, this system of detection with two types of sensitive elements in the same sensor, allows to make redundant the detection of two equal gases or to detect at the same time two different gases in chemical and petrochemical plants, in the industry of converting and stocking liquid and gaseous hydrocarbons or industries for conversion into other fuels like hydrogen, ammonia and the like.

BRIEF DESCRIPTION OF THE DRAWINGS

The system described in the present invention will be illustrated in detail by means of the accompanying drawings and their description, where only some possible innovative embodiments are described, in which:

FIG. 9 is a table showing some possible combinations of detections effected by the innovative sensors of the further innovative system according to the present invention.

DETAILED DESCRIPTION OF THE INVENTION

Figure 1:
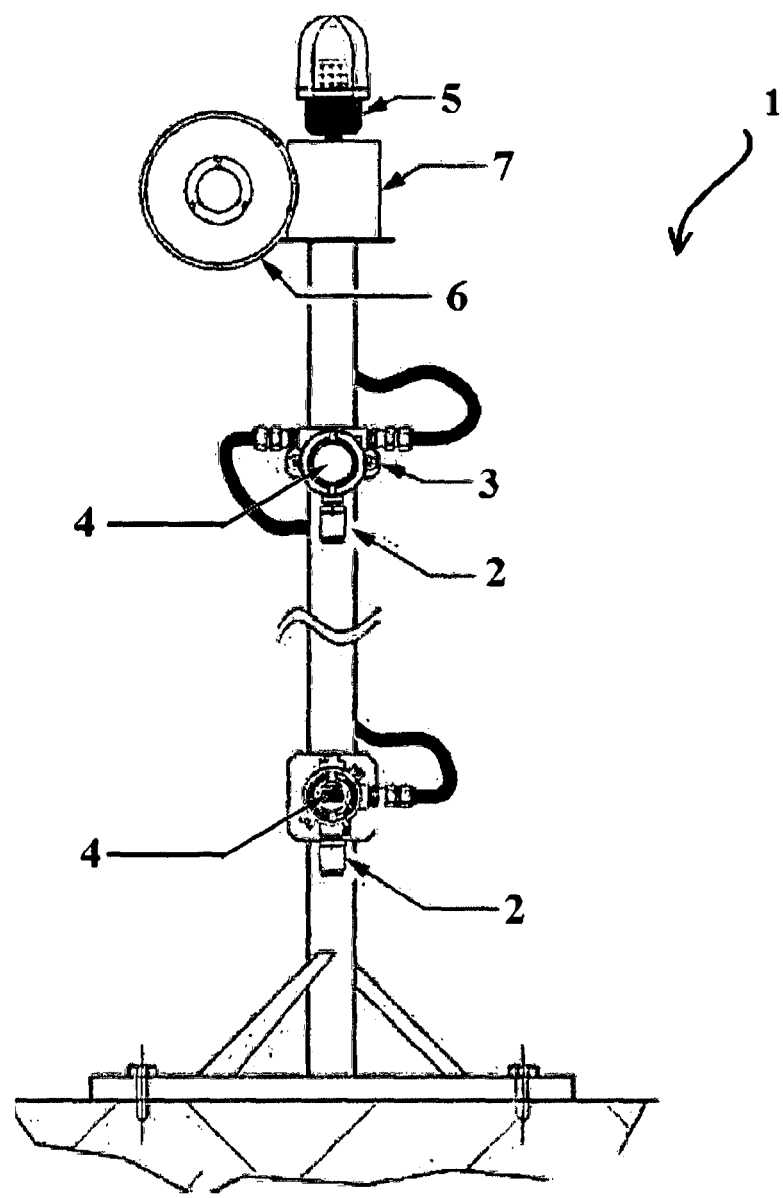
FIG. 1 shows an example of an embodiment of the complete system, illustrating a gas detection system according to the present invention in more detail.

With reference now to FIG. 1 of the drawings, a detection system 1 according to the present invention is shown, for instance installed on column or like piece, comprising at least in this embodiment, at least a remote transducer for detecting gases heavier than air, at least a transmitter 2 with double channel 3, in this example advantageously disposed at an ergonomic height to make easier reading and servicing operations, comprising at least one display 4 to show the gas survey (in this case according to the object of the present invention, there are more displays to monitor two or more gases, as one can see in the detail of FIG. 9), a light signal system 5 such as a gas alarm flashlight, at least an acoustic signal 6 such as a gas alarm siren, and a junction box 7.

More particularly it is to be noted that the transducer is incorporated into the sensor body where the sensitive element is directly connected through a plug and play system, i.e. a plug-in connection adapted to generate a strong signal (e.g. through an electric variation) when contacted with a specific gas or a gas family, as illustrated. It is to be noted that there are several types of transducers, referred to also as sensitive elements, for the individual or simultaneous detection of different categories of gases (such as e.g. hydrocarbons containing flammable and toxic gases) with different types of transducers inserted into the same housing, where in a particularly preferred embodiment Applicant mentions as example the sensor individually certified according to the norms Atex-IECEx. These classifications and seats or housings are implemented in classified areas, allowing to obtain simultaneously a double measurement of the same gas, or of different gases simultaneously present in the air, in order to warrant that in every condition the detection of a dangerous gas in the air is effected and remote signalled to the personnel and the safety officers.

The sensitive elements and the transducers 2 connected as above indicated, are generally fixed to a thermally insulating support, and are provided with a device keeping the temperature constantly over 5° C. for outdoor temperatures up to −55° C. (−67° F.).

Having advantageously at disposal an innovative transmitter with single channel or two independent channels, and the possibility of remote installation of any sensor with one sensitive element or two sensitive elements with the same or different technology, the connection with the transmitter is now simple, because the transducer incorporated in the sensor generates a strong signal adapted to cover distances up to 300 meters. This allows the installation of the transmitter at an ergonomic height, in order to make easier the operations of reading, servicing and calibrating the device and positioning the sensor as close as possible to the source of risk. This advantageous feature allows a plurality of possibilities of remote installation, since for instance it is possible to mount a sensor of combustible gas, using a sensitive element of the IR type, directly connected to the transducer, and from the latter directly to the transmitter positioned on the top portion of the installation column; a sensor of this kind is for instance adapted for methane detection; the same transmitter is used for connection to the remote sensor, e.g. with a sensitive element of the type Nano-MOS, installed at the base of the installation column for detection of gases heavier than air such as H2S.

According to this example of installation, it is possible to mount on the same column a system of light signal 5 and an acoustic alarm 6 to alert personnel of the local danger.

Figure 2:
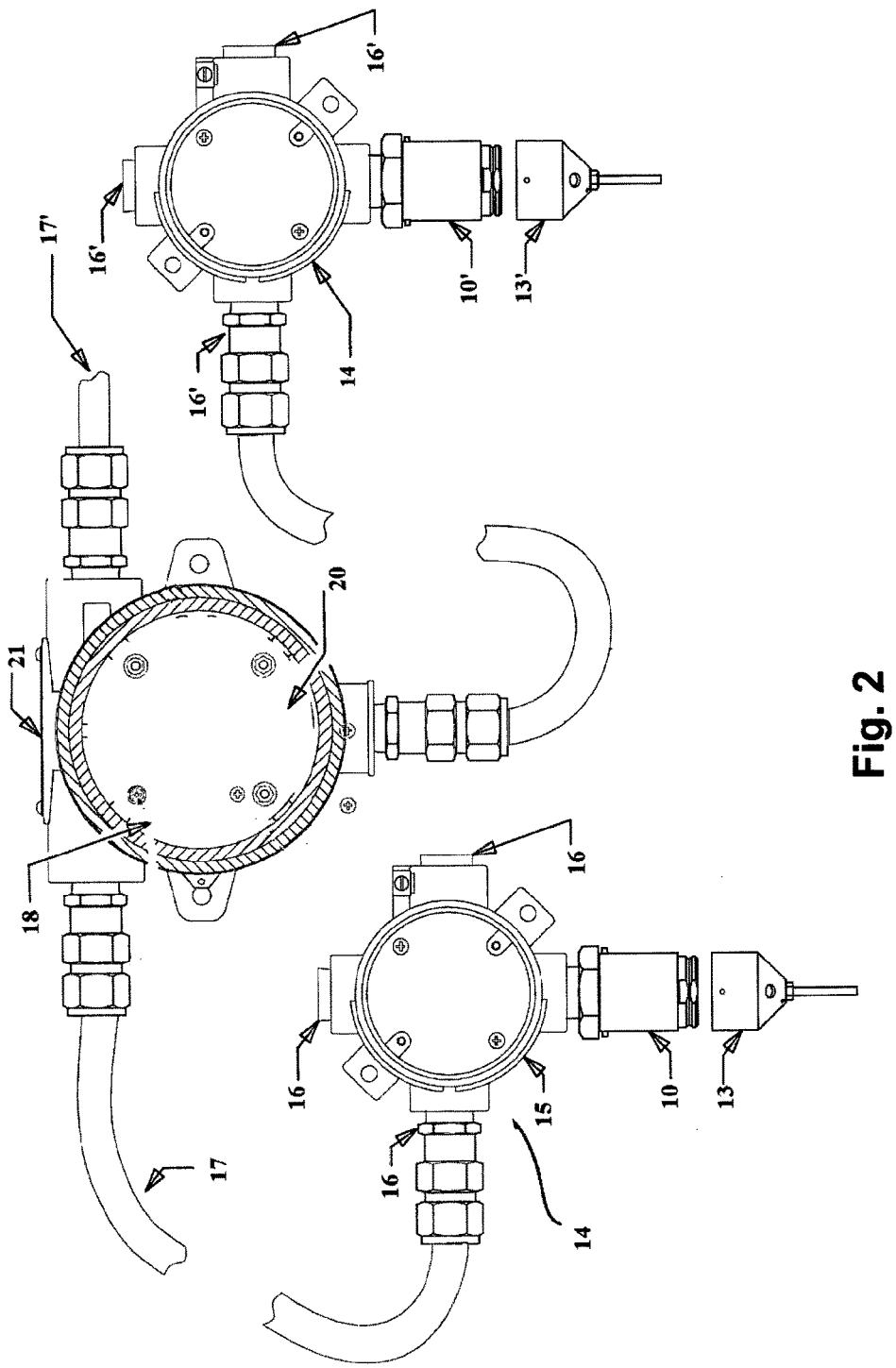
FIG. 2 shows an embodiment of the innovative system according to the present invention in an exploded broken view of the technical assembly.

With reference now to FIG. 2 and the related following description, it is to be pointed out that the object of the detection system according to the present invention, includes also an innovative electronic circuit, of which the following is an exemplary description not limiting the scope of protection of the present invention. All the electronic circuits of the chain of detection, transmission, indication and measurement, receiving and transmitting signals from sensors on the spot containing transducers and sensitive elements (e.g. electrochemical or physical elements) of type PP plug and play, were designed with components of most advanced technology based on the new "1-Wire" Transmission Technology. The basis of the 1-Wire transmission is a serial protocol using a single data baseline plus mass reference for the communication. The advantages are low consumption, low voltage and less electronic components with consequent greater reliability. This technology allowed to connect sensitive elements having six wires like the infrared cells used for aerospace applications, with three wires drastically reducing time and cost of sensors and obtaining function check in CRC (cycling redundancy check) through a proprietary protocol. Each 1-Wire cooperates in master and slave devices with an exclusive unalterable proprietary protocol implemented by Applicant on 64 bits ID which is used as address generator to be transmitted on 1-Wire bus. 1-Wire master and slave operate with an electric feeding voltage of 2.8 VDC assuring minimum power and minimal dimensions of cables. These innovative transducers are provided with intelligence on board of the microprocessor protected and inerasable with annexed firmware and software applicative program to allow recognition of type of sensitive element connected and preset the output signal to the transmitter according to the standard parameters of the presently in force international norms. In order to further increase safety, a recognition system was created, where the possible change of transducer or sensitive element with another type of technology, is signalled as fault and inhibits the measurement, signalling the kind of fault on the transmitter display and to the control room, while the complete system does not undergo any damage. The replacement of the type PP sensitive element may advantageously be effected live, i.e. without disconnecting feed from the system and does not require any electric instrumental operation, as it is simply sufficient to position the equipment magnet on the transmitter display. This operation inhibits the connection transmitter/sensor, allowing all the operations of replacement of the sensitive element, cleaning or replacement of filter in a maximum time of three minutes, at the end of which by repositioning the magnet on the transmitter display, the electronic system initiates the sequence of self-diagnosis of the entire electronics, ending in 30 seconds, showing four zeros on the display front panel and lighting a green LED on the front panel, to indicate that the gas sensor detection system and the transmitter are aligned and operative.

Figure 3A:
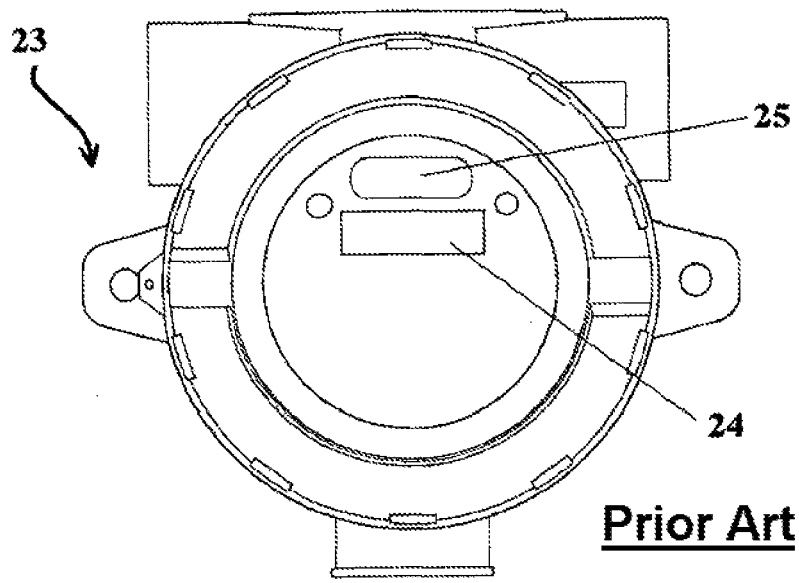
FIG. 3 show a single channel display (3a) compared with an innovative multi-channel display (3b)
Figure 3B:
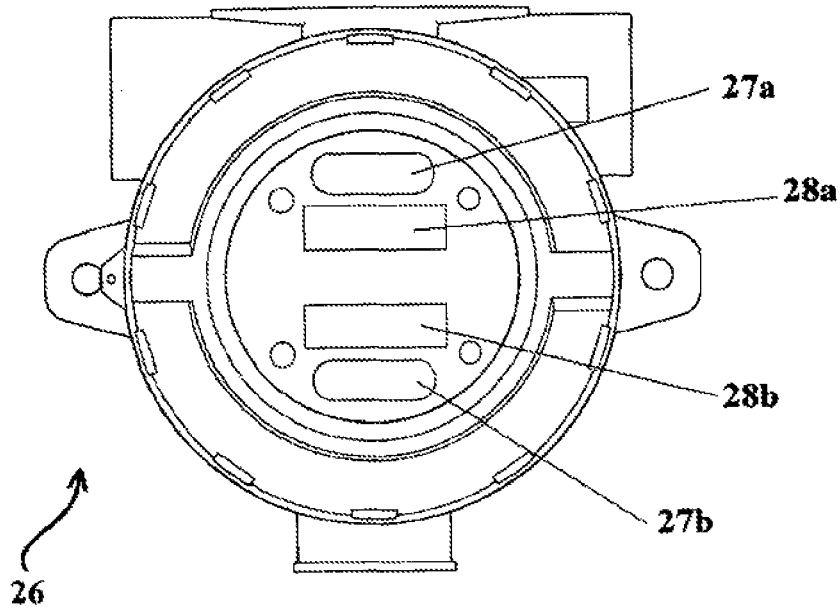

It is to be noted that for clarity reasons, it was opted for the description of a particularly preferred embodiment of a portion of the detection system according to the present invention, in order to give the technical operative details required for the description of the system, but they merely constitute the means to achieve the object of the innovative detection system with two or more channels being the subject matter of the present invention, wherein FIG. 2 shows a remote transducer 100 with two detection channels, in an exploded view of the main parts and their interconnection. In the present particularly advantageous embodiment, two transducers 10, 10' are connected to the required assembling related components, including protection elements 13, 13' for said transducers 10, 10', said transducers being connected to a detection body 14, 14' comprising at least a junction box 15, 15', connection and earthing couplings 16, 16' and connection cables 17,17' to connect both transducers 10, 10' advantageously to the double channel transducer 18 for detection of two or more flammable and/or toxic gases and their combinations. Said double channel transducer comprises a display 20 (illustrated in greater detail in FIG. 3) and at least a transmitter 21. It is to be noted that in the detailed views of FIG. 3, FIG. 3*a* shows a prior art single channel display 23 monitoring on a digital display 25 the signal emitted by the corresponding gas and including an indicator 24 of the type of detected gas. FIG. 3*b* shows an innovative advantageous double channel display 26, thus comprising at least one display 27 *a* with related indicator 28 *a* of gas type for a channel 1, and at least a corresponding display 27 *b* with related indicator 28 *b* of gas type for a channel 2.

Figure 4:
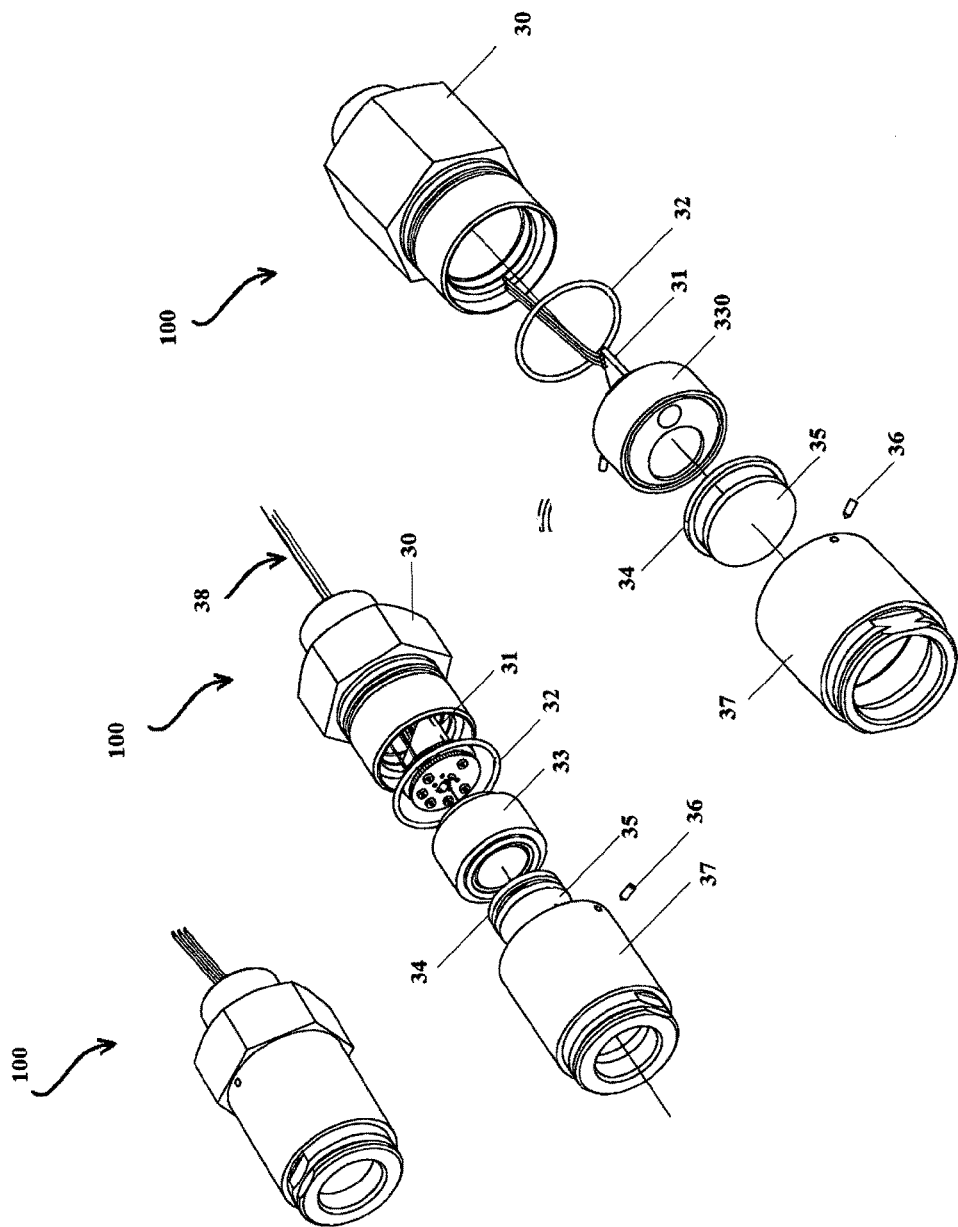
FIG. 4 shows an exploded and assembled view of the innovative system in a preferred embodiment of the invention.

With reference now to FIG. 4, showing an innovative transducer 100, in both assembled and exploded view, in a preferred embodiment of the present invention, more particularly said transducer 100, at least as main components of interest for the system according to the present invention, generally comprises a sensor body 30 with related removable cover (that may be varied as to form and dimensions according to the specific applications), a customized designed electronic transducing circuit 31 (which varies according to the implementation requirements and as discussed hereinbefore), sealing elements 32 like for instance O-rings, at least one plug-in member 33 with single or double transducer or even a plug-in insertion body 330 with multiple transducers, then connected to ring(s) 34 for at least one filter 35, which in a particular advantageous way may be replaced according to the objects of the invention, a locking member 36 for covering the sensor, and a removable cover 37 for said sensor. Obviously cover 37 as well as the sensor body 30 are variable according to the specific application. More particularly the sensor body 30 was designed with a movable filter holder 35' allowing to remove it without detaching wires or connection elements 38, or disconnecting power feed to the instrument. In practice, having substantially decided to be able to replace sensitive elements even with active current feed, generally referred to as HFR (Hot Field Replacement), filter 35 is for this purpose inserted in cover 37 of the sensor body 30, that can be easily cleaned or disassembled when it is necessary to replace it or the sensitive element 33, so that in the course of the same operation it is possible to check the sintered filter 35 and if required said filter may be cleaned in a very advantageous way, simply taking it out of its housing. Obviously filter 35 may be cleaned in any moment during the operations of checking and calibrating the gas detector. This is particularly advantageous with reference to the previously mentioned dangerousness of filter clogging, the difficulty of checking said clogging, the impossibility of replacement and the high cost of replacement for the prior art devices.

The implementation of the system according to the present invention required also to design again the transducer and the electronic transmitter, which as previously noted is coupled to the independent single or double channel field sensors, implemented for instance on printed circuit boards of the multilayered kind, e.g. with SMD (surface mounting device) components connected to the single or double micro-LED numeric display or LED displays to monitor locally data detected by the field sensor or sensors, and to transmit them to the control room, generally located in a remote and safe area.

In a particularly advantageous way this allows not only to use a single operator for handling, servicing and calibrating the device, when the sensor is integrally fixed with the transmitter, but allows also to carry out these operations when the sensor is remote installed through the calibrator. Another innovative feature in the construction of these new sensors, in a particularly advantageous way, is that they may be installed substantially up to 300 meters away from the signal universal transmitter, while the infrared and electrochemical sensors presently available on the market, have a strong transmission limitation of few meters only of distance from the transmitter. Taking into account that in a gas escape, both flammable and toxic gases are often present, use of the double channel transmitter allows to connect both the sensor for flammable gases and the sensor of toxic gases at the same place, by positioning the sensor for light (flammable) gases generally lighter than air, in the ergonometric position, that is at eye's level, while the sensor of toxic gases is positioned at a lower level on the same support, at about half a meter from the floor (see the annexed drawings).

Figure 5:
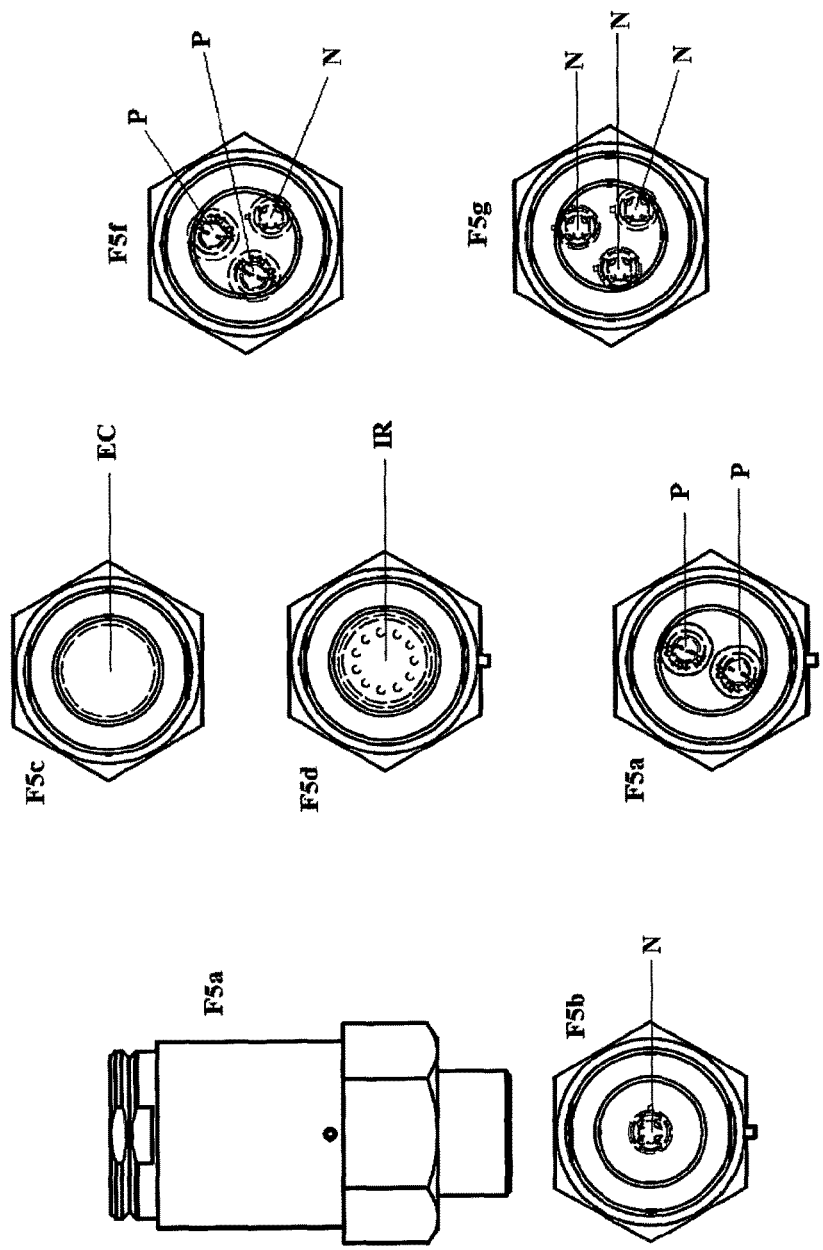
FIG. 5 shows innovative sensors of the present invention in the dual technology format, i.e. double detection technology.
Figure 6:
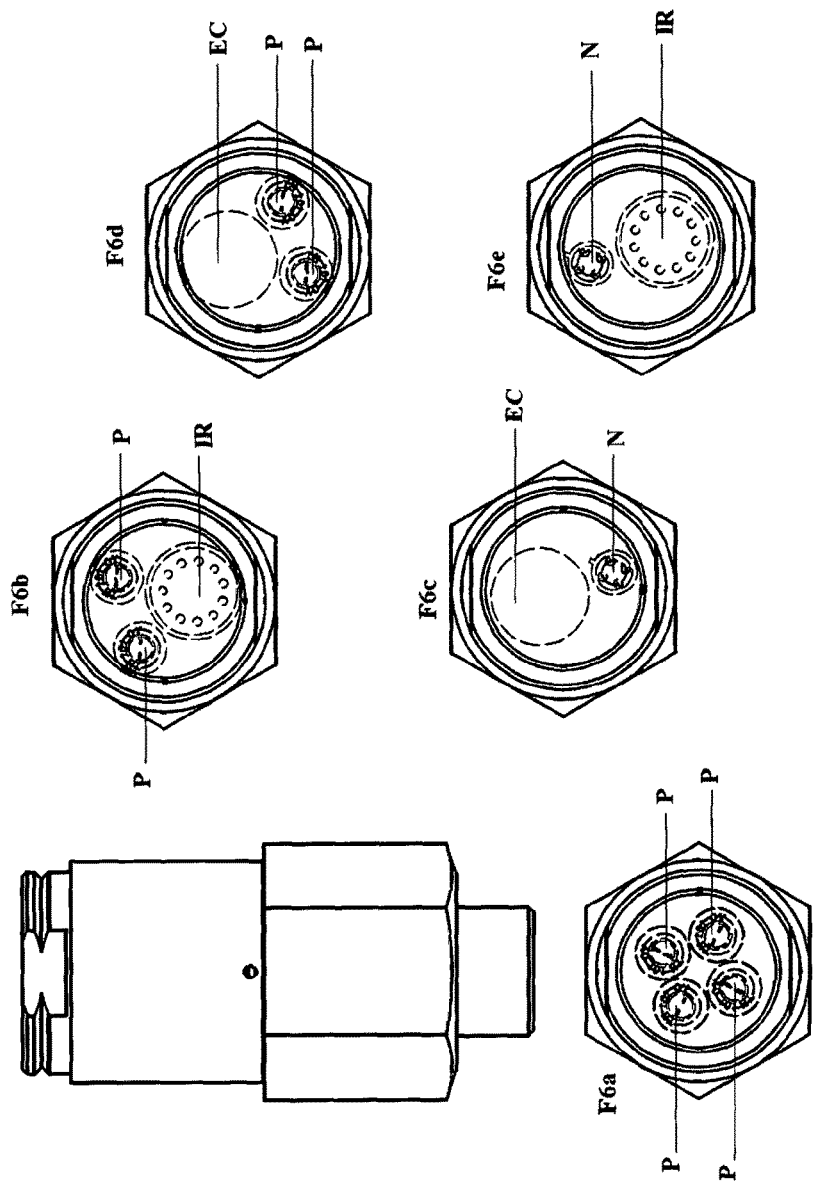
FIG. 6 and FIG. 7 show said innovative sensors in the medium and large format, respectively, according to the required application.
Figure 7:
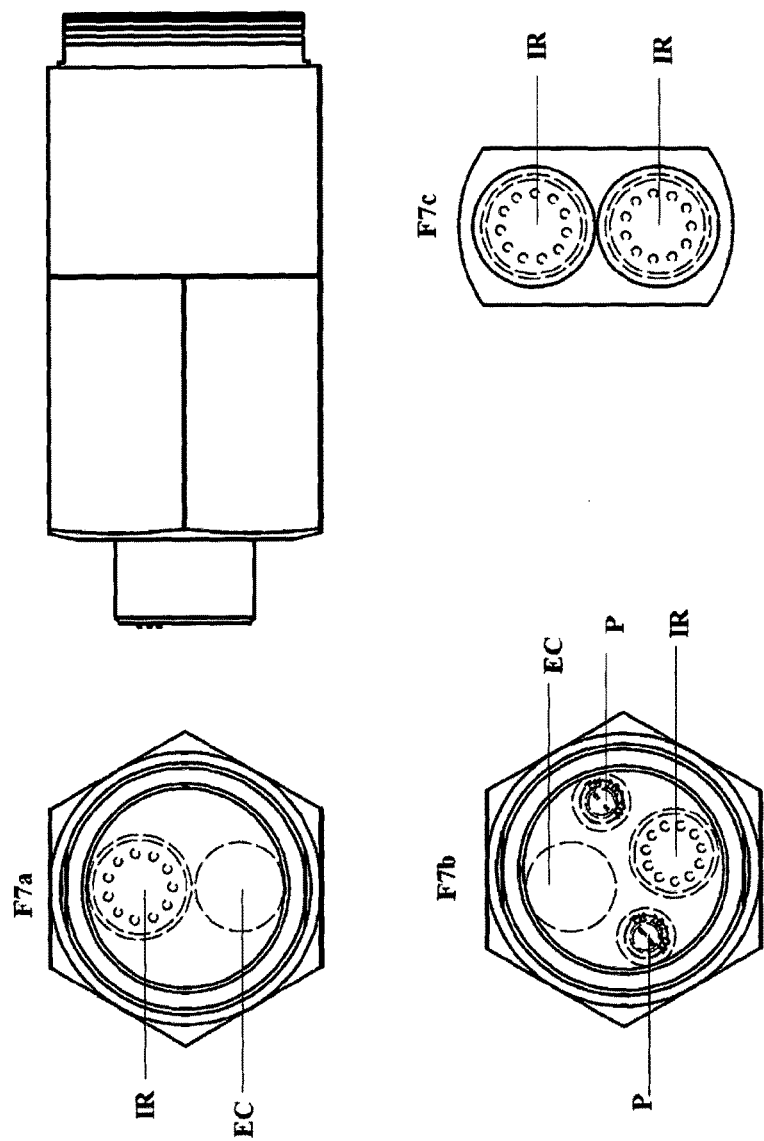

Again, with reference to FIGS. 5, 6, 7 of the drawings, several alternative embodiments of innovative gas sensors according to the present invention are illustrated, wherein in FIGS. 5*a* and 5*b* the assembled sensor body is shown in a side view and FIG. 5*b* an example of sensor for toxic gases with nano-MOS sensitive element.

Just for comparison FIGS. 5*c* to 5*e* show prior art sensors for the subsequent clear comparison with the innovative sensors of the following figures, wherein FIG. 5*c* shows an electrochemical sensor for toxic gases with related electrochemical sensitive element, FIG. 5*d* an infrared sensor with related IR sensor, and FIG. 5*e* a combustion sensor for combustible and flammable gases with pellistor (e.g. consisting of a resistive element) acting as a sensitive element. FIG. 5*f* on the contrary shows an innovative double technology sensor, including for instance two pellistors P and a nano-MOS sensitive element, which therefore is adapted to recognize toxic and combustible gases and consequently is a combined catalytic and nano-MOS sensor. In addition, FIG. 5*g* shows another embodiment of said sensor, in this case for toxic gases, with triple recognition.

FIG. 6 shows further possible embodiments for the innovative sensor of the present invention, wherein said embodiments concern sensors with double or triple technology. FIG. 6*a* shows an embodiment of the innovative sensor with double technology of medium size, namely a redundant catalytic sensor for flammable gases including for example one plus one pellistors; FIG. 6*b* shows a combined catalytic sensor including two pellistors and an infrared IR detector for detection of flammable gases and hydrocarbons; FIG. 6*c* shows a redundant sensor including one electrochemical EC and one nano-MOS NM sensitive element; FIG. 6*d* shows a combined catalytic and electrochemical sensor for flammable and toxic gases; and finally FIG. 6*e* shows a combined nano-MOS NM and infrared IR sensor for toxic gases and hydrocarbons.

Finally, FIG. 7 shows the innovative sensor according to the present invention in a so-called big format. In these embodiments, FIG. 7*a* shows an infrared IR detector and an electrochemical sensitive element forming a combined electrochemical/infrared combined sensor; FIG. 7*b* shows in a still more advantageous way a triple technology, namely an electrochemical sensitive element, an infrared detector and two pellistors, constituting a combined electrochemical/catalytic/infrared sensor for the detection of toxic gases, flammable gases and hydrocarbons. FIG. 7c shows a version of a sensor with a particular format (demonstrating that there are numerous embodiments not limited to those presently illustrated, that as already pointed out are simple implementing examples) of the redundant kind for hydrocarbons, comprising at least two infrared detectors.

Figure 8A:
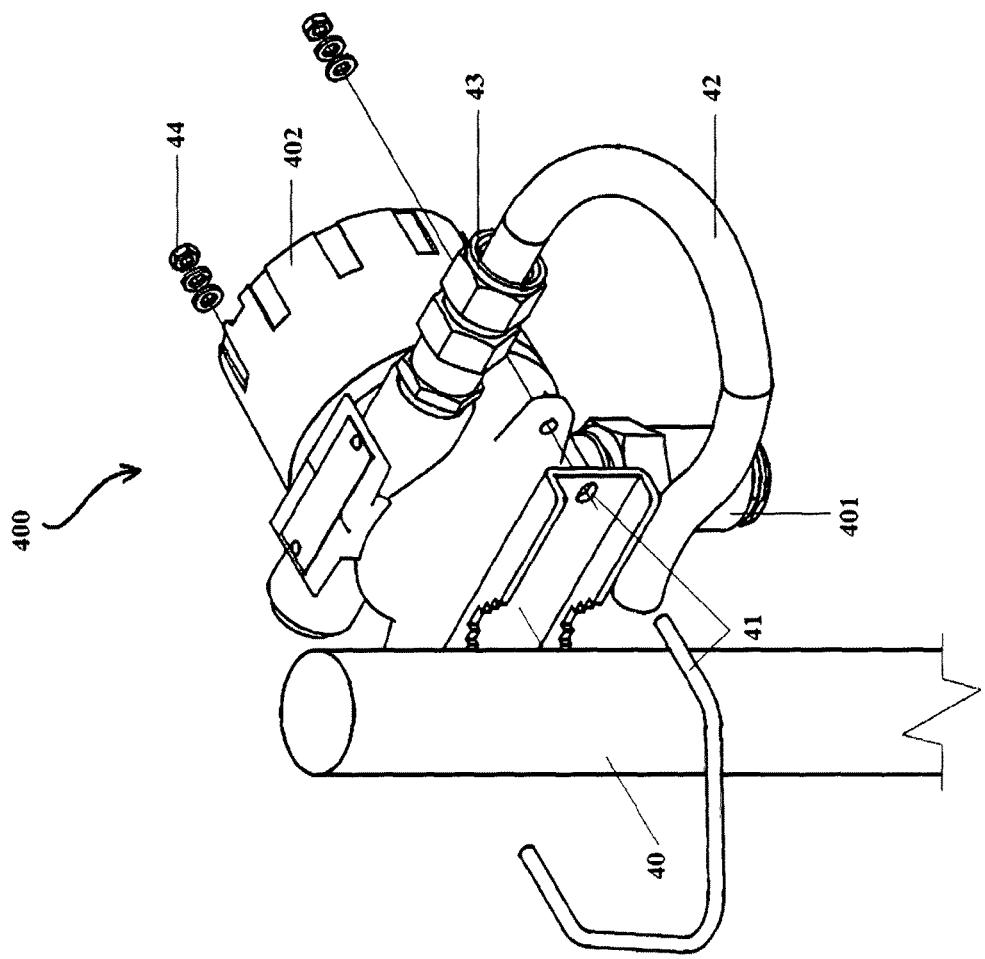
FIG. 8a shows a preferred embodiment of the detection system of the present invention, when fixed for instance to a rod or pole.
Figure 8B:
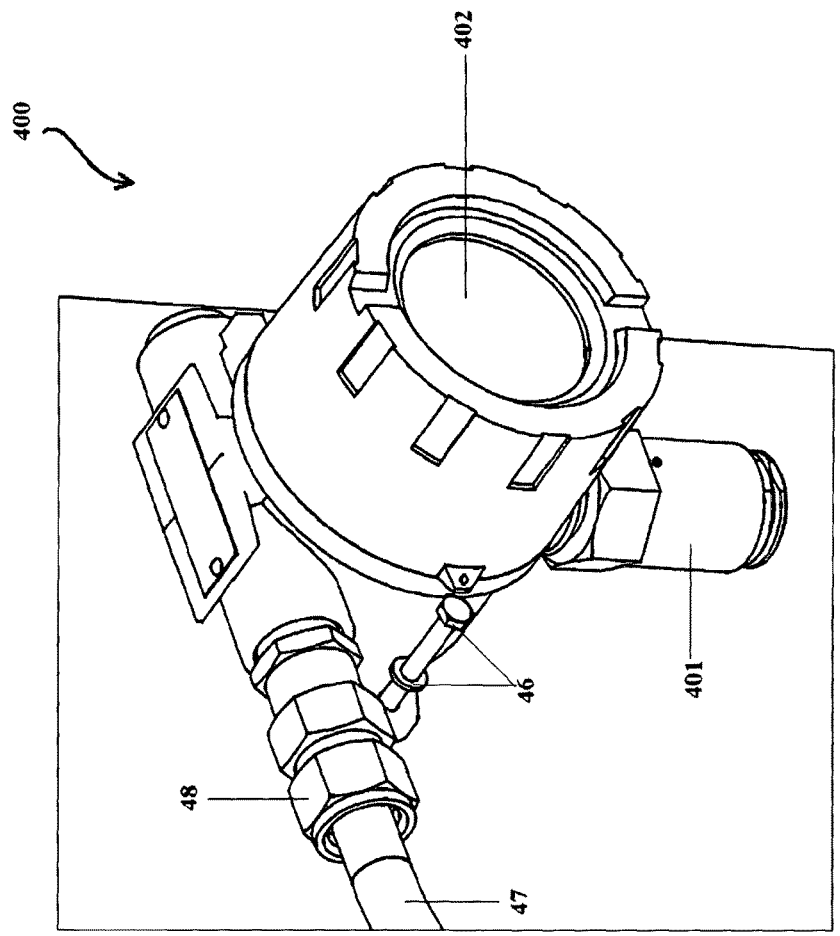
FIG. 8b shows the essential portion of the detection system of the present invention, when fixed to a wall.

FIGS. 8a and 8b show two examples of standard assembling of gas detection systems, with the particular system of the present invention; FIG. 8a shows an assembling kit 41 for mounting on a pole 40, with the detail of the transducer 401 connected to the body of the detection system 400 and the rear view of the transmitter 402, with standard details, such as fastening means 44 and cable 42 with cable holder 43. FIG. 8b shows the same embodiment of the detection system 400, but here for fixing to wall 46. It is to be noted that said system 400 is advantageously adapted for any kind of assembly, provided that the system has a suitable kit for the intended use, and by adopting some simple contrivances possibly for transferring coupling and/or assembling places, for instance of cable 47 with cable holder 48 or other corresponding elements that according to the positioning place may easily have different positions relative to the couplings.

For sake of completeness the annexed FIG. 9 is a table showing some particularly preferred embodiments of possible combinations of the innovative sensors according to the present invention.

Finally the advantageous multitechnological sensor according to the present invention is provided with a splash guard allowing to be installed outdoor even in place with problems of bad weather or with working fire fighting apparatus.

A complementary fitting of the technological innovation of the new gas sensor for the here described innovative system, is a set of vertical support stakes provided with rain protection roof, where sensors and transmitter may be installed in the same place but in different positions according to the kind of flammable and/or toxic gases, taking into account their particular specific weight. This solution allows also to obtain redundancy of the detection point so as to increase reliability of the measurement and to connect two kind of sensors with different technology and application on the same support together with all the auxiliary devices in order to alert the operators of the detected imminent danger, locally by means of sirens, loudspeakers, flashing lights. The solution achieved by the here described gas detectors, allows to improve safety of operators and plants and also to obtain a considerable reduction of installation costs and increase of reliability of the alarm systems for protection of operators.

Use of gas detectors with several integrated sensors and transmitters is the optimal solution for the total protection of platforms, rigs and plants for extraction of gas and oil, constituting high risk environments, assuring a higher reliability and at the same time an economy on a large scale with the implementation of an integrated system consisting of the stake for the installation of the components of the system of detection, alarm and alert all included in a single solution. These features are non-renounceable conditions in high risk plants like those with presence of toxic and/or explosive gases and consequent danger of fire.

The innovative detection system of the present invention generally provides and comprises at least the following listed elements:

At least a sensor body that may contain one, two or three sensitive elements of the same technology or different technologies, or for different gases and technologies for generating signals related to various gases present at the same time.

Contemporaneous operation of different sensitive elements or sensors of the same type, but redundant to achieve a greater reliability of the detection system.

Connection of the various sensors to a double channel transmitter showing the two readings at the same time on two independent displays, in order to assure a better detection to protect the area interested by escape of toxic and/or explosive gas.

The sensitive elements may be replaced live by application of a magnet on the display and insertion (plug-in extraction and insertion) without de-energizing the sensor.

The possibility to clean or replace the sintered filter (that may be made for instance of stainless steel 316L) during the routine servicing or for an arisen need due to dust clogging e.g. after a weather disturbance.

Sensitive elements comprising transducers integral with smart electronics to recognize the type of connected sensitive element, and transforming the signal according to the detected physical variable selected in advance for the system, said smart electronic system sending a signal to the transmitter which in turn feeds the system with powers required by the various components.

Possibility to transform the signal into a standard value, e.g. 4-20 mA according to the norms in force.

Communication with the external world or surrounding environment through a serial connection e.g. on a pair with RS 485 modbus or other protocols such as Hart and so on.

The transmitter specially designed to meet the requirements of said innovative gas detection system, that is then designed and made e.g. with SMD components, in order to receive at least two independent electric signals from a two channel multiple sensor or two independent single sensors, and to generate two independent feeds with two outputs of different valve, the one for the transmitter and the other for the sensor.

And in addition, in order to implement a feasible embodiment:

one or more digital displays with four digits micro LEDs or LED indicators for conventional signalling such as at 4-20 mA, a circuit with three solid state relays, for signalling through electric connections the pre-alarm, alarm and fault conditions, serial communication Modbus, serial communication Hart, RS 485, transmitter housing and sensor housing with independent and associated certifications according to norms ATEX IECEx (or a housing for installations in areas classified in the various classes of danger of presence of explosive gases or mixtures).

It is to be noted that each element with specific nomenclature or order of magnitude of data transmission is being reported here as a mere example of particularly preferred embodiments of the innovative gas detection system described by the present invention.

Additional variations in which the system elements are coupled in different ways, by opposition of parts, engagement or coupling of the elements, or alternative assemblies of the system elements, such as different embodiments of transducers or alternative position of one or more filters, as well variations to the detection system in the parts not strictly relevant for the innovative system described in the present invention, should be considered an object of the present invention.

For instance, alternative forms of the detection elements, like rounded, rectangular, hexagonal and other forms, are not relevant for the manufacturing and protection purposes of the object of the present invention, even in case of alternative forms or positions, but in any case suitable for the objects of the invention, or any kind of materials, or any modification falling in any case within the object of the invention, are all to be considered alternative embodiments to the preferred ones previously described, in which modifications and changes concerning for instance the geometries selected for the various movable and fixed elements, the materials adopted for each member, and even the specifications of the operative system, or modifications and adjustments of software, may be resorted to without departing however from the scope of protection of the present invention as defined in the appended claims.

The invention claimed is:

1. A system for detection of toxic and/or flammable gases, the system comprising:
   at least a transducer including at least a sensor body, an electronic circuit, a plug-in body for housing one or more sensitive elements, and a filter, wherein the one or more sensitive elements are of the same type of technology or of different technologies, suitable for generating a gas detection signal for each sensitive element, and
   a transmitter to transmit signals generated by said transducer by means of said sensitive elements to a display, said transmitter being connected via said transducer to said sensitive elements, said transmitter comprising a transmission technology that communicates by employing a serial protocol using a single data baseline plus mass reference over at least two or more independent channels suitable for signalling the detection of a single gas type in redundant way, or of more than two types of gas contemporaneously in case of gas mixtures, said system being arranged to show at the same time said gas detection signals on said display and wherein said filter being replaceable by a user in case of the filter fouling or clogging.

2. The system for gas detection according to claim 1, wherein said sensor body, sealing elements between an electronic circuit, said plug-in body and at least said filter and covers, are removable at least during the calibrating and cleaning operations.

3. The system for gas detection according to claim 1, wherein said filter is disposed in a removable way between said plug-in body and a removable cover.

4. The system for gas detection according to claim 1, wherein said filter may be replaced as a single component or cleaned by removing the sensor body.

5. The system for gas detection according to claim 1, wherein said sensitive elements of the same type of technology, are suitable for working simultaneously in a redundant way for a greater system reliability, or said sensitive elements of different type of technology are suitable for working simultaneously for sensing different kinds of gases, or said sensitive elements are suitable for working in a triple way with the operative logic two out of three.

6. The system for gas detection according to claim 5, wherein said electronics are suitable for sending a signal to said transmitter, which in turn is suitable for feeding the system with the power required for the operation of the various components of said system.

7. The system for gas detection according to claim 1, wherein said transmitter is suitable for transmitting signals corresponding to each gas detected so as to show at the same time said detection signals on one or more displays, or on one or more indicators.

8. The system for gas detection according to claim 1, wherein said sensitive elements comprise electronics installed on board to allow recognition of the type of sensitive element that is connected to the transducer, in order to transform the signal to be transmitted according to the detected quantity.

9. The system for gas detection according to claim 8, wherein said transmitter is suitable for generating two independent feeds with at least two outputs of different value, of which the one is for said transmitter and the other for said at least one transducer and sensitive element.

10. The system for gas detection according to claim 1, wherein said transmitter is suitable for connecting one or more independent circuits from one or more sensor bodies with at least two sensors or from two independent sensitive elements.

11. The system for gas detection according to claim 1, wherein said sensitive elements are electrochemical, or infrared type or combustion type, or a combination of two or more types of said sensitive elements, or nano-mos semiconductor for toxic gases, or with catalytic combustion or thermal paramagnetic for combustible/flammable gases and also a combination of one or more types of said sensitive elements for the contemporaneous detection of different gases of both combustible/flammable gases and toxic gases.

* * * * *